United States Patent [19]
Quandt

[11] 3,963,019
[45] June 15, 1976

[54] OCULAR TESTING METHOD AND APPARATUS

[76] Inventor: Robert S. Quandt, 8 Darby Lane, Deerfield, Ill. 60015

[22] Filed: Nov. 25, 1974

[21] Appl. No.: 526,851

[52] U.S. Cl. .............................. 128/2 T; 128/2 A; 356/39
[51] Int. Cl.² .......................................... A61B 5/00
[58] Field of Search ............ 128/2 A, 2 L, 2 T, 2 E, 128/2.1 E; 351/9; 356/39–41, 51

[56] References Cited
UNITED STATES PATENTS

| | | | |
|---|---|---|---|
| 2,893,288 | 7/1959 | Sheridan | 128/2 T |
| 3,412,729 | 11/1968 | Smith, Jr. | 128/2 L |
| 3,463,142 | 8/1969 | Harte | 128/2 L |
| 3,638,640 | 2/1972 | Shaw | 128/2 L |
| 3,648,685 | 3/1972 | Hepp, et al. | 128/2 L |

OTHER PUBLICATIONS
*Nature,* vol. 214, June 3, 1967, pp. 986–988.
*California Medicine,* June 1963, vol. 98, No. 6, pp. 325–327.
*Diabetes,* vol. 21, suppl. 2, 1972, pp. 703–712.

*Primary Examiner*—Kyle L. Howell
*Attorney, Agent, or Firm*—Johnson, Dienner, Emrich & Wagner

[57] ABSTRACT

A method and apparatus for detecting changes in body chemistry, for example, glycemia, is disclosed in which a beam of light is projected into and through the aqueous humor of the patient's eye. An analyzer positioned to detect the beam on its exit from the patient's eye compares the effect the aqueous humor has on said beam against a norm. An excess or deficiency of glucose present in the aqueous humor produces a corresponding positive or negative variation in the exiting beam and thereby indicates a hyper or hypo glycemia condition in the body chemistry of the patient being tested.

11 Claims, 4 Drawing Figures

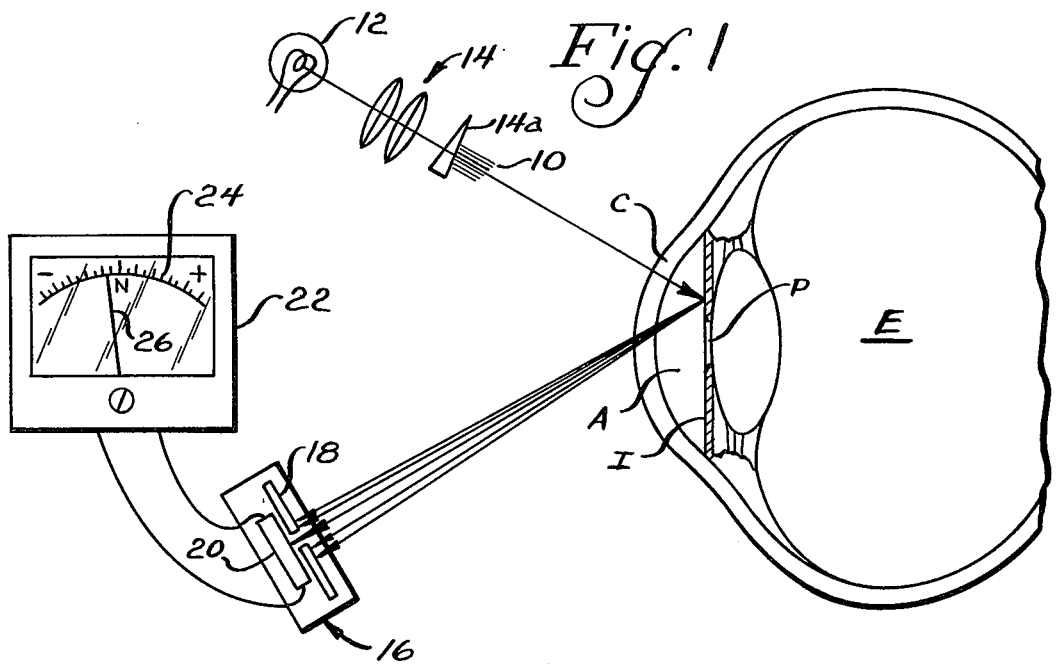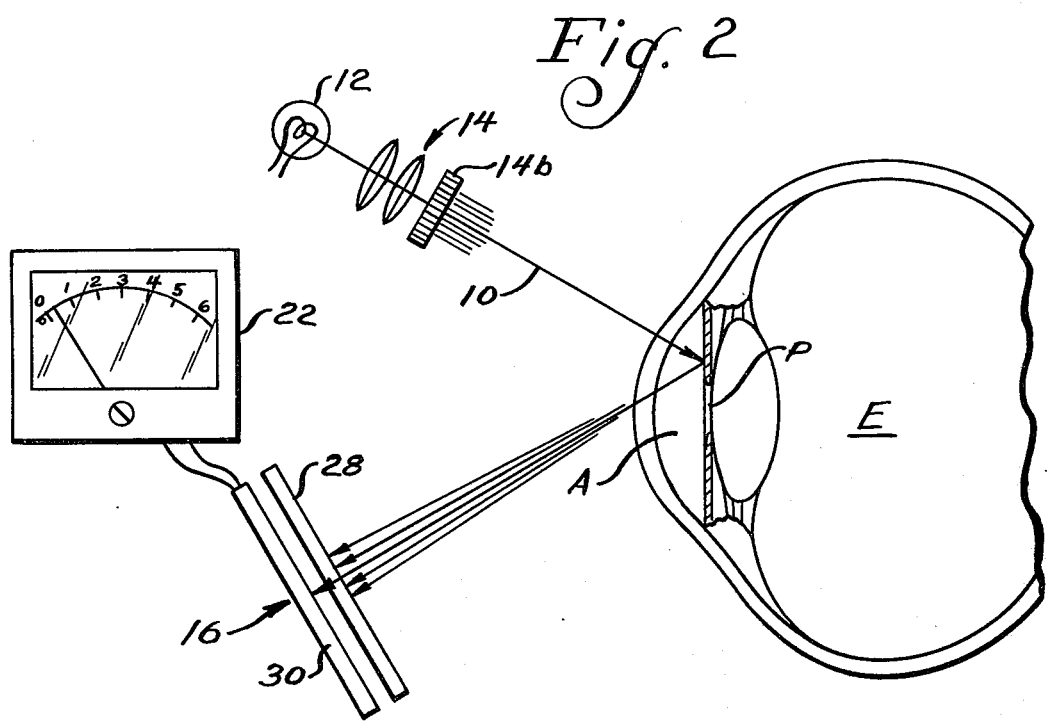

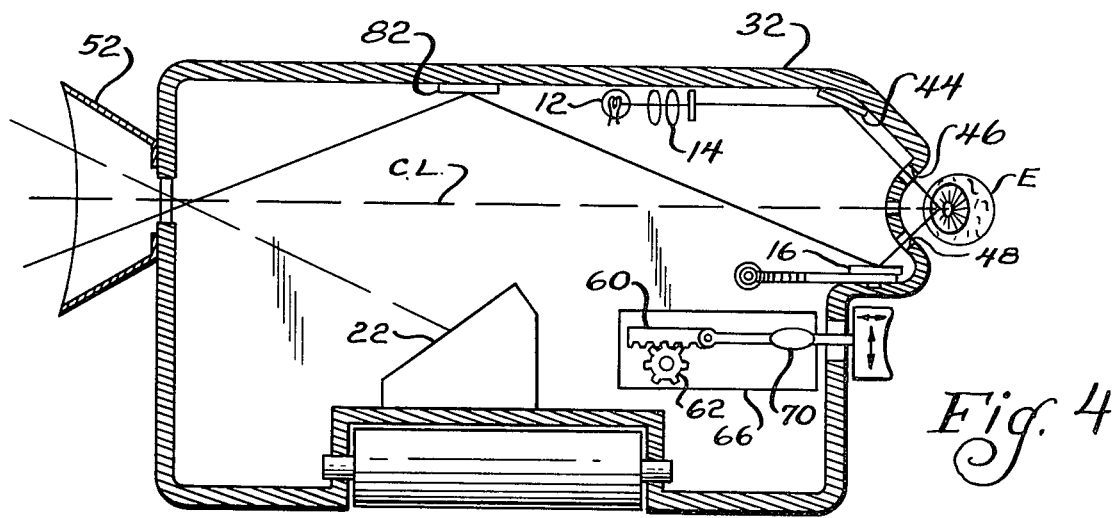
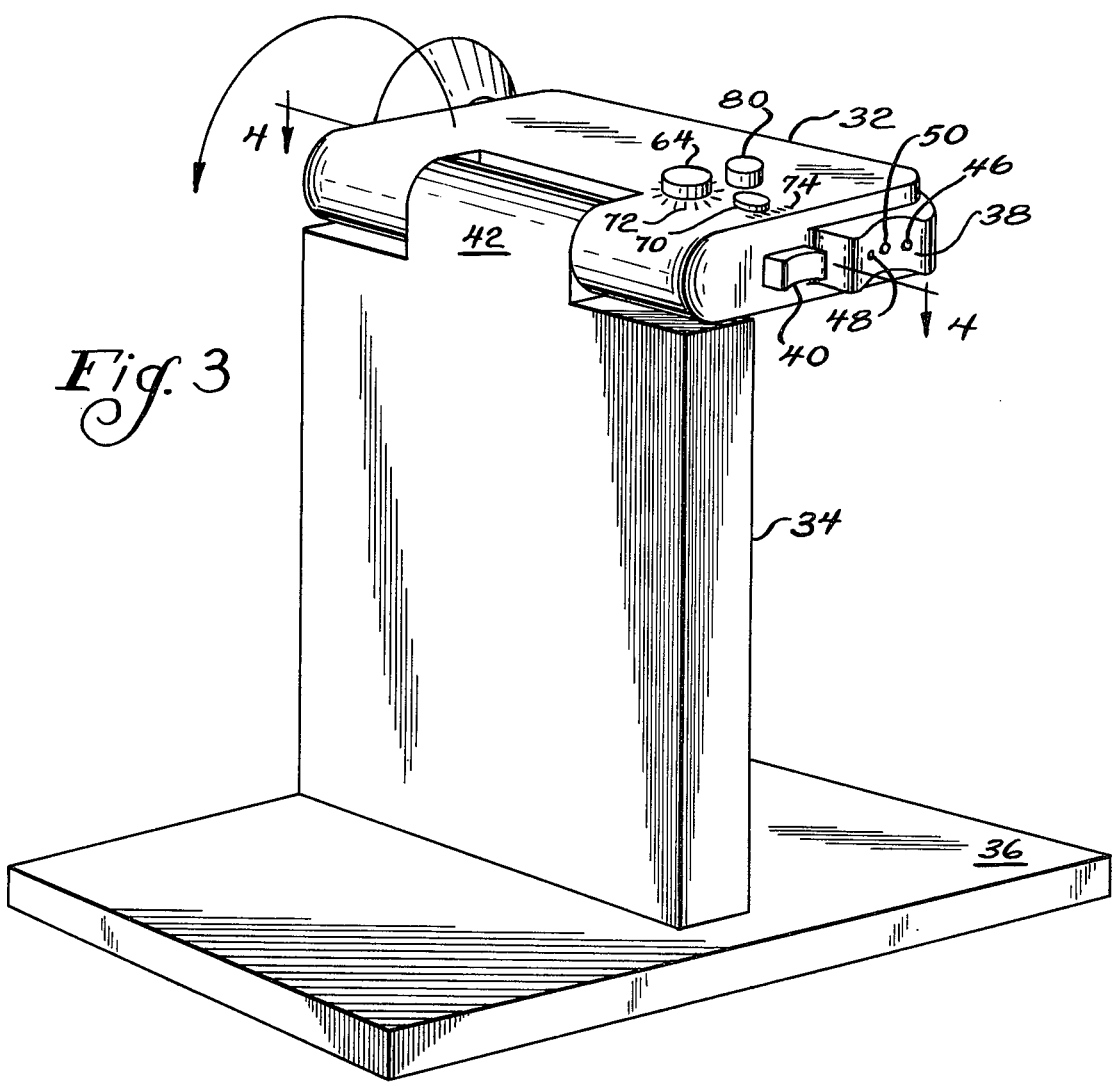

OCULAR TESTING METHOD AND APPARATUS

This invention relates to novel means and methods for detecting changes in body chemistry. Although not limited thereto, the invention is particularly useful in testing a patient for hyper and hypo glycemia, as in the diagnosis and/or treatment of diabetes mellitus.

Prior to the present invention, such tests were commonly conducted by taking a specimen of the body fluids, urine and/or blood, and running a test on the specimen to measure, for example, its sugar content.

The present invention improves upon such earlier methods by providing improved means and method for detecting an abnormality in the body chemistry which requires neither preparation of the patient nor a sample of the patient's body fluid on which to conduct an analysis or test.

The invention takes advantage of the fact that changes in the chemistry of the human or animal body are evident in the eye fluids and usually show up in the eye fluids first. Thus a principal object of the invention is to provide means and method by which variations from a norm in the body chemistry can be detected optically.

It is known that the eye fluids including both the vitreous humor and aqueous humor have a refractive index of 1.337 which approximates that of glucose whereas the cornea has a refractive index of 1.377 which is only slightly greater than that of the aqueous humor. It is also known that a beam of polarized light when projected through a sucrose-containing solution will be rotated by an amount proportional to the concentration of sucrose in the solution. Also, light, and particularly a collimated beam of light, when passed through such a solution, will be refracted from its original path proportional to the amount of sucrose present in the solution.

The present invention utilizes such phenomena to provide novel apparatus and/or methods in which a beam of light is projected into the patient's eye so that it enters the aqueous humor and passes therethrough outwardly of the eye to a suitably positioned analyzer which detects or measures the effect of the changed chemistry, for example glucose content of the aqueous humor thereon. In its presently preferred form the light beam is directed at an angle such that on entering the aqueous humor of the patient's eye it strikes the iris to one side of the pupillary area and is reflected outwardly of the eye to an appropriately positioned analyser. The beam may be one of polarized light in which event the analyser comprises means to measure the angle through which the polarized light is rotated. In an alternate arrangement, means such as a refractometer is utilized to measure the change in refraction which the glucose effects. In accordance with the invention, the amount of displacement (rotation or refraction) of the reflected beam received by the analyzer is compared with a standard, for example an expected rotation or refraction when the glucose content of the eye fluid is normal. The reading may be taken either visually or electrically as afterwards explained. A "plus" or "minus" reading also can be used to indicate a hyper or hypo glycemic condition in the patient's body chemistry, as the case may be.

Thus a feature of the invention is that no samples of body fluid are required to conduct the test. The test is clean and convenient to conduct; and the results of the test are instantaneously available.

The invention is particularly useful in the diagnosis of various body ills, such as diabetes mellitus of which an excess or deficient glucose content in the body chemistry is indicative; however, it is also useful, for example, in the detection of a diabetic tendency. This is because a sugar change in the body chemistry initially shows up in the eye fluids and prior to the development of an actual diabetic condition. The present invention therefore provides convenient means for early detection of a diabetic condition or tendency and before it would be noticed using more conventional testing methods of which the inventor is presently aware.

Variations in the composition of a patient's body chemistry other than its glucose content can also be detected by means of the invention so as to be useful in the diagnosis and/or detection of the patient's susceptibility to ailments other than hyper or hypo glycemia. For example, the invention can be used to detect enzymes emitted by a diseased or malfunctioning body organ, as for example the pancreas. It can also be utilized to detect other than normal amounts of components making up the body chemistry including ions such as calcium and sodium and certain salts when present in the aqueous humor which differently affect a light beam passed through the aqueous humor by utilizing an analyzer capable of measuring the effect of said enzymes, ions, salts or other composition of the body chemistry on a light beam passed through the aqueous humor of a patient's eye.

Thus the invention provides novel body chemistry testing apparatus having the advantages and/or features that it can be made compact, can be conveniently operated and the results of which can be read instantaneously. Thus the invention has particular utility over previously known testing methods and apparatus or means.

Many other objects and advantages, as well as features of the invention will be at once apparent or will become so upon consideration of the presently preferred embodiments of the invention which now will be described.

Referring therefore to the drawings wherein embodiments of the invention for carrying out the method thereof are illustrated:

FIG. 1 is a schematic diagram illustrating a first mode of the invention wherein a beam of collimated light is utilized;

FIG. 2 is a schematic diagram illustrating a second mode of the invention which utilizes a beam of polarized light;

FIG. 3 illustrates one form of apparatus in which either mode of the invention illustrated by FIGS. 1 and 2 may be utilized; and FIG. 4 is a cross sectional view of said apparatus, taken along lines 4—4 of FIG. 3 and illustrates one arrangement of the components within the apparatus housing.

Referring now more particularly to the several views wherein like parts are considered to be identified by like reference numerals, FIG. 1 illustrates a first embodiment of the invention which is suitable for detecting a hyper or hypo glycemia condition in the patient's body chemistry. Such an embodiment comprises a suitable light source 12 and a lens system 14 which includes a collimating prism 14a for projecting a beam 10 of collimated light from the light source into the eye E of the patient under test. As illustrated, collimated light beam 10 is directed at a selected angle such that it strikes the cornea C of the patient's eye, passing through the cornea into the aqueous humor A to impinge on the iris I to one side of the pupil area P and is reflected outwardly of the eye again passing through the aqueous humor A and cornea C. Alternatively, light source 12 may be so located that light beam 10 passes through the aqueous humor without striking the iris. At 16 is an analyzer such as a refractometer or spectrometer positioned to receive the reflected beam of collimated light 10 on its exit from the patient's eye E. In passing through the aqueous humor of the patient's eye light beam 10 is refracted from its original path proportionate to the concentration of, for example glucose present in the aqueous humor.

In FIG. 1 analyzer 16 is illustrated as comprising a movable optical slit 18 fixed forwardly of a photocell 20 connected to a voltmeter 22. As is well known, optical slit 18 may be adjusted to adapt the analyzer to measure the intensity of a particular wave length of refracted light which strikes the photocell 20 behind the optical slit 18. As illustrated, voltmeter 22 is provided with a scale 24 relative to which an indicator 26 moves in response to the amount of light impinging on the photocell 20. Voltmeter 22 is so set that indicator 26 will point to N centrally of scale 24 when the intensity of light impinging on photocell 22 is normal, that is when the intensity of said light corresponds to that expected as a consequence of refraction of the light beam by the aqueous humor of an eye containing a normal concentration of glucose. When the aqueous humor contains less than a normal amount of glucose, indicator 26 shifts to the minus side of the scale so as to indicate a hypo-glycemic condition. Conversely, deflection of the indicator to the plus side of the scale will indicate an excess of glucose present in the aqueous humor or hypo-glycemic condition in the patient's body chemistry. By means of the graduations of scale 24, a numerical value can be set for the hyper or hypo glycemic condition indicated.

A reading of the glucose content in the aqueous humor and thereby the existence of a hyper or hypo glycemic condition in the patient's body chemistry may also be obtained by projecting a monochromatic polarized beam of light into the patient's eye, and measuring the angular displacement which the glucose content of the aqueous humor effects on the polarized light beam as said beam passes therethrough and is reflected out of the eye thereto. One such arrangement is illustrated in FIG. 2. Referring to said FIG. 2, the arrangement is generally similar to FIG. 1 except that the collimating prism 14a of lens system 14 has been replaced by a plane polarizer 14b which, for example, may be a dichroic dyed disc of molecularly oriented plastic. Optical slit 18 of analyzer 16 also has been replaced by a second plane polarizer 28. As in the first described embodiment, a beam of polarized light 10 is projected through the aqueous humor A of the patient's eye or to one side of the pupil area P so as to be reflected by the iris portion I outwardly through the aqueous humor to the analyzer 16. Polarized light beam 10 as it passes through the aqueous humor of the patient's eye will not only be refracted, as above explained, but its axis of polarization is rotated in proportion to the glucose content thereof. Thus, in FIG. 2 the existence of an abnormal concentration of glucose in the patient's body chemistry can be determined and also measured by comparing the angle through which the second plane polarizer 28 must be adjusted to produce a darkened field on screen 30 which is located behind the polarizer 28. If polarizer 28 is rotated to place its axis at right angles to the axis of the polarized light exiting from the patient's eye, no light passes through the polarizer 28 and screen 30 is dark. If polarizer 28 has been rotated to an angle previously determined to be at right angles to the angle through which the polarized light passing through the aqueous humor of a patient's eye having a normal amount of glucose, then the absence of light on screen 30 indicates a normal glycemic condition in the patient's aqueous humor and thereby his body chemistry. However, if the body chemistry of the patient under test contains an excess or deficiency of glucose, then screen 30 will be lighted because this corresponding excess or deficiency in the aqueous humor will cause the polarized beam passing therethrough to be differently rotated, and the analyzing polarizer 28 will allow some portion of the light beam to pass. A lighted screen 30 is therefore indicative of an abnormal sugar content in the body chemistry and the intensity of that light is indicative of the extent of said abnormality.

As illustrated in FIG. 2 screen 30 may also comprise a photocell connected to voltmeter 22 as in the FIG. 1 embodiment which measure the amount of change in light intensity impinging on 30, and therefore the change in glucose content of the aqueous humor in the eye of the patient under test. If polarizer 28 is set at some angle other than that necessary to completely cut off all light exiting from the patient's eye when the aqueous humor contains a normal amount of glucose then, as in the case of FIG. 1, voltmeter 22 will respond to light impinging on the photocell to indicate whether the patient's body chemistry contains a hyper or a hypo glycemia condition, and the position of the voltmeter indicator relative to its scales serving to place a value thereon.

FIGS. 3 and 4 illustrate a preferred form of apparatus in which the invention may be utilized. As shown in FIG. 3, such apparatus comprises a housing 32 in which is supported the light source 12, lens system 14 and analyzer 16, as well as voltmeter 22. Preferably, housing 32 is mounted on an upright 34 provided with a base 36 by means of which the apparatus may be set on a table or desk with the patient and operator seated to opposite sides thereof. As illustrated, housing 32 is provided with a patient's eye piece 38 on its forward side and also a nose rest portion 40 against which the patient may rest his head to aid in aligning his eye with the eye piece 38. Housing 32 may be rigidly fixed to upright 34 or it may be suitably hinged thereto as illustrated at 42 in FIG. 3. In the latter event, the housing 32 may be swung on the axis of hinge 42 to either side of upright 34 so that eye piece 38 may be optionally used to check either of the patient's eyes.

Referring now to FIG. 4, it will be seen that the housing provides support for light source 12, as well as lens system 14, which are shown mounted within the housing to one side of center line CL. A first mirror provided at 44 directs the projected light beam 10 from lens system 14 through opening 46 in eye piece 38 so as to enter the eye E of a patient properly aligned with said eye piece 38. Eye piece 38 also contains a second opening 48 through which the light beam passes on exit from the patient's eye E and is directed to the analyzer 16. As illustrated in FIG. 4, eye piece 38 also includes a central opening 50 between light entrances 46, 48 which is centered with the pupil of the patient's eye. For this purpose, opening 50 is shown on center line CL as is also a second eye piece 52 through which the operator views opening 50 and the patient's eye therebehind to properly align the patient's eye to receive the projected light beam and reflect it as above described. In order to assist the patient in stabilizing the required alignment of his eye E with openings 46, 48 of eye piece 38, the aforementioned nose rest 40 is made adjustable in directions both axially of center line CL and transversely thereof. FIG. 4 illustrates nose rest 40 as supported at one end of a gear rack 60 which is movable axially in a direction parallel to the center line CL by a drive pinion 62 rotated by externally located knob 64 (FIG. 3) to which it is connected. Gear rack 60, drive pinion 62 and its operating knob 64 are shown mounted on a suitable slide 66 which is adjustable laterally on guides (not shown) toward and away from the center line CL to locate the nose rest 40 at the proper spacing from the patient's eye under test. Suitable means in the form of externally located lever 70 may be utilized to effect said lateral movement of slide 66. It will be understood that housing 32 will be suitably slotted to accommodate said adjustment. For example, the apertures in housing 32 through which the connecting stem of knob 64 to pinion 62, as well as the portion of the forward wall of the housing 32 through which gear rack 60 extends are sufficiently enlarged or elongated to accommodate said lateral movement. Operating knob 64 and finger piece 70 are illustrated in FIG. 3 as located on the top surface of housing 32 where they may be conveniently actuated by the operator as he continues to view the patient's eye through eye piece 52. Suitable graduations 72, 74 are shown associated with both finger piece 70 and operating knob 64 so that the adjusted positions of the nose rest 40 can be recorded for use in subsequent testing of the patient. Once the apparatus has been properly aligned with the patient's eye as above described, a test for glycemia may be conducted by either of the previously discussed methods therefor and the results noted.

In the event the apparatus of FIGS. 3 and 4 is utilized to house the method represented by FIG. 1, it will be understood that lens system 14 includes the colliminating lens 14a aforedescribed and that optical slit 18 may be preset to receive an elected wavelength of light. Suitable means may also be provided for adjusting the same which, for example, may be under the control of externally located knob 80. Volt meter 22 may be located either externally or internally of housing 32. In FIG. 4 it is shown mounted within the housing and at an angle so that its indicator 26 and scale 24 are visible to the operator looking through eyepiece 52. A suitably inclined mirror at 82 may be utilized to permit the operator's viewing of analyzer to assist in its adjustment.

In the event housing 32 is used to house the embodiment represented by FIG. 2, it will be understood that lens system 14 will include the aforementioned plane polarizer 14b. In this event, it will be understood that analyzer 16 will comprise the aforementioned second plane polarizer 28 and screen 30 spaced therebeneath as previously described. In this event, the externally located knob 80 may be suitably operatively connected to polarizer 28 by means such as a pinion and worm gear to permit its rotation by the operator. In this event, also, mirror 82 may be suitably angled so that an image of the analyzer screen will be visible in reflection to an operator looking at the mirror through eye piece 52. As previously explained, screen 30 also may comprise a photocell connected to voltmeter 22.

Under some circumstances, it may be advantageous to close down the pupillary area P of the patient's eye under test so as to increase the area behind the aqueous humor against which light beam 10 may be directed. For this purpose light from an auxiliary light source (not shown) may be directed through opening 50 of eye piece 38 during the test.

Although not specifically illustrated, it will be understood that other variations and/or arrangements of the optical system illustrated by FIGS. 1 and 2 and the apparatus illustrated by FIGS. 3 and 4 may be employed in the practice of the invention. For example, in place of the desk-mounted apparatus illustrated by FIGS. 3 and 4, housing 32 may be adapted as a handheld instrument. It also may be provided with two pairs of eye pieces which are aligned with the respective two eyes of the patient. Either or both of these eye pieces may have an optical system aligned therewith to permit the operator to optionally conduct the test using either one or both eyes of the patient. Under normal circumstances testing of one eye, however, will suffice.

Also, in the embodiments described, analyzer 16 has been considered as adapted for measuring the displacement of the light beam as it is refracted (FIG. 1) or its polarization axis is rotated (FIG. 2) by the glucose content of the aqueous humor of the eye under test. Where light beam 10 is passed through the aqueous humer of the patient's eye for detecting variations in the body chemistry other than glucose, it will be understood that an analyzer 16 will be selected that is capable of measuring and/or detecting the effect on the light beam which the component of the body chemistry under test produces thereon as the light beam passes through the aqueous humor.

Thus, as described, it will be apparent that all of the recited objects, advantages and features of the invention have been demonstrated as obtainable in a highly practical manner.

Having described my invention, I claim:

1. Apparatus for detecting changes or variations in a patient's body chemistry comprising means for projecting a beam of plane polarized light through the aqueous humor of a patient's eye, the aqueous humor containing a chemical which rotates the polarization axis of the light beam as it passes therethrough in proportion to the amount of said chemical present in the aqueous humor, and an analyzer positioned to be impinged by said exiting beam of light, said analyzer including means for measuring the angle through which the polarization axis of the light beam has been rotated.

2. Apparatus for detecting a hyper or hypo glycemic condition in the aqueous humor of a patient's eye comprising a housing having a reference member to which a patient aligns his eye, a light source spaced from said reference member, a lens system for directing a beam of light from said light source to the reference member so as to enter a patient's eye aligned therewith, pass through the aqueous humor and exit from the eye, and detector means positioned to receive the light beam as it exits from the patient's eye, the light beam being changed by changes in the glucose content of the aqueous humor as it passes therethrough so as to differently impinge upon the detector means, said detector means including indicator means which respond to different impingements of the light beam thereon so as to indicate a hyper or hypo glycemic condition.

3. Apparatus as claimed in claim 2 wherein the lens system includes means for plane polarizing the beam of light, the polarization axis of the light beam being rotated by the glucose content of the aqueous humor as it passes therethrough, and the analyzer means comprising a pair of superposed aligned plane polarizing discs, one of said discs being rotatable relative to the other to measure the angle through which the polarization axis of the light beam has been rotated.

4. Apparatus as claimed in claim 2 including means for locating the patient's eye relative to said reference member.

5. Apparatus as claimed in claim 4 wherein the locating means includes an adjustable nose engaging portion.

6. Apparatus as claimed in claim 4 wherein the locating means includes sighting means and means for centering the patient's eye therewith.

7. Apparatus as claimed in claim 2 wherein the detector means comprises an adjustable optical slit for selective passage of light, a photocell position to receive light passed by the optical slit, and a voltmeter connected to the photocell for measuring the intensity of the light impinging on the photocell.

8. A method of testing for a hyper or hypo glycemic condition in the human body comprising the steps of quantitatively measuring the glucose content of the aqueous humor of a patient's eye by directing a beam of light through the aqueous humor, the light being displaced from a norm consequent to an excess or deficiency of glucose present in the aqueous humor, and detecting the amount of displacement of said light beam as it exits outwardly from the eye.

9. The method of claim 8 wherein the beam of light directed through the aqueous humor of the patient's eye has been polarized and it is the axis of polarization of the light beam that is displaced by the glucose.

10. The method of claim 9 including the further step of measuring the angle through which the polarized light is rotated by the glucose content of the aqueous humor.

11. The method of claim 8 wherein it is the refraction of the light beam that is changed by the glucose content of the aqueous humor and the method includes the further step of measuring the change in refraction of the exiting light.

* * * * *